United States Patent
Pal et al.

(10) Patent No.: US 8,774,473 B2
(45) Date of Patent: Jul. 8, 2014

(54) ATTENUATION CORRECTION OF MR COILS IN A HYBRID PET/MR SYSTEM

(75) Inventors: Debashish Pal, Richmond Heights, OH (US); Zhiqiang Hu, Twinsburg, OH (US); Chia-hua Tung, Aurora, OH (US); Tianrui Guo, Richmond Heights, OH (US); Jeffrey Kaste, Chagrin Falls, OH (US)

(73) Assignee: Koninklijke Philips N.V., Eindhoven (NL)

(*) Notice: Subject to any disclaimer, the term of this patent is extended or adjusted under 35 U.S.C. 154(b) by 463 days.

(21) Appl. No.: 13/148,053

(22) PCT Filed: Jan. 18, 2010

(86) PCT No.: PCT/IB2010/050218
§ 371 (c)(1),
(2), (4) Date: Aug. 5, 2011

(87) PCT Pub. No.: WO2010/097714
PCT Pub. Date: Sep. 2, 2010

(65) Prior Publication Data
US 2011/0317900 A1    Dec. 29, 2011

Related U.S. Application Data

(60) Provisional application No. 61/155,169, filed on Feb. 25, 2009.

(51) Int. Cl.
*G06K 9/00* (2006.01)
*A61B 6/00* (2006.01)
*G01T 1/16* (2006.01)
*A61B 6/12* (2006.01)
*A61B 6/03* (2006.01)
*A61B 5/055* (2006.01)
*G01R 33/48* (2006.01)
*G01T 1/164* (2006.01)

(52) U.S. Cl.
CPC .......... *G01T 1/1648* (2013.01); *A61B 6/5294* (2013.01); *G01T 1/1603* (2013.01); *A61B 6/5205* (2013.01); *A61B 6/12* (2013.01); *A61B 6/5247* (2013.01); *A61B 6/5258* (2013.01); *A61B 6/037* (2013.01); *A61B 5/055* (2013.01); *A61B 6/4417* (2013.01); *A61B 6/032* (2013.01); *A61B 6/58* (2013.01); *G01R 33/481* (2013.01); *A61B 6/5235* (2013.01)
USPC .......................................... 382/128; 382/168

(58) Field of Classification Search
CPC ............. G01T 1/1603; G01R 33/4801; G01R 33/4808
See application file for complete search history.

(56) References Cited

U.S. PATENT DOCUMENTS

| | | | |
|---|---|---|---|
| 6,201,247 B1 | 3/2001 | Lutheran et al. | |
| 7,923,691 B2 | 4/2011 | Ladebeck | |
| 2007/0221850 A1* | 9/2007 | Panin et al. | 250/363.04 |
| 2009/0105583 A1* | 4/2009 | Martin et al. | 600/422 |
| 2010/0074501 A1* | 3/2010 | Ladebeck et al. | 382/131 |
| 2010/0135559 A1* | 6/2010 | Morich et al. | 382/131 |
| 2011/0123083 A1* | 5/2011 | Ojha et al. | 382/131 |

FOREIGN PATENT DOCUMENTS

| | | |
|---|---|---|
| DE | 102008022816 A1 | 12/2009 |
| JP | 6308243 A | 11/1994 |
| WO | 2008135873 A1 | 11/2008 |

OTHER PUBLICATIONS

Bai, C., et al.; A Generalized Model for the Conversion From CT Numbers to Linear Attenuation Coefficients; 2003; IEEE Trans. on Nuclear Science; 50(5)1510-1515.

Hofman, M., et al.; MRI-Based Attenuation Correction for PET/MRI: A Novel Approach Combining Pattern Recognition and Atlas Registration; 2008; J. of Nuclear Medicine; pp. 1875-1883.

Hofman, M., et al.; Towards quantitative PET/MRI: a review of MR-based attenuation correction techniques; 2009; Eur. J. Nucl. Med. Mol. Imaging; 36(Suppl 1)S93-S104.

Hubbell, J. H.; Photon Cross Sections, Attenuation, Coefficients, and Energy Absorption Coefficients From 10 keV to 100 GeV; 1969; NSRDS-NBS 29; 85 pages.

Karp, J. S., et al.; Singles transmission in volume-imaging PET with a 137Cs source; 1995; Phys. Med. Biol.; 40:929-944.

Kops, E. R., et al.; Alternative Methods for Attenuation Correction for PET Images in MR-PET Scanners; 2007; IEEE Nuclear Science Symposium Conference Record; M26-112; pp. 4327-4330.

Kops, E. R., et al.; Template-based attenuation correction of PET in hybrid MR-PET scanners; 2008; J. Nucl. Med.; 49 (supplement)162p.

Zhang, B., et al.; Attenuation correction for MR table and coils for a sequential PET/MR system; 2009; IEEE Nuclear Science Symposium Conference Record; pp. 3303-3306.

Schlemmer, H-P., et al.; Simultaneous MR/PET Imaging of the Human Brain: Frasibility Study; 2008; Radiology; 248(3)1028-1035.

\* cited by examiner

*Primary Examiner* — Anand Bhatnagar
*Assistant Examiner* — Soo Park (57) ABSTRACT

Nuclear image data generated by a multimodal imaging device, such as a combined position emission tomography (PET)/magnetic resonance (MR) scanner (12, 14), is attenuation-corrected with a combined patient-specific attenuation correction (AC) map and an AC map template (70) for an MR coil (72) that is present in both the nuclear and MR scanning procedures. A template library (46) contains templates for each of a plurality of MR coils and other accessories. Each template is generated on one of two manners. The coil may be imaged inside the PET scanner 14 with the transmission source 16 (e.g., Ge-68 or Cs-137). A transmission image 48 is reconstructed using the known algorithms and may be used as the AC template directly. Alternatively, the template can be generated by creating a global histogram of the transmission image and identifying segments of the coil or other accessory. An average linear attenuation coefficient (LAC) value is determined from the distribution of the histogram. The coil or other accessory is imaged using a high resolution CT scan, and the CT image is segmented and assigned the computed LAC values determined from the distribution of the histogram to create the AC map template for the coil.

22 Claims, 8 Drawing Sheets

ATTENUATION CORRECTION OF MR COILS IN A HYBRID PET/MR SYSTEM

CROSS REFERENCE TO RELATED APPLICATIONS

This application claims the benefit of U.S. provisional application Ser. No. 61/155,169 filed Feb. 25, 2009, which is incorporated herein by reference.

The present application finds particular utility in medical imaging systems. However, it will be appreciated that the described technique(s) may also find application in other types of imaging systems, other attenuation correction systems, and/or other medical applications.

Positron emission tomography (PET)/magnetic resonance (MR) hybrid systems use MR scans for attenuation correction of PET images. In PET/MR, the patient attenuation map is developed based on the MR images. The MR patient image is segmented, the various tissues and organs identified, and appropriate attenuation coefficients are applied. Different local MR coils are used for high resolution MR images of different parts of the body. Some coils are attached to a patient support or table, and others are attached to the patient. When employing a dual mode PET/MR scanner, the table and coils are present in the scanner during the PET data acquisition. Although it was originally believed that the MR coils would be sufficiently radiation-transparent, such that attenuation correction would not be needed, it has been determined that this is not the case. Rather the MR coils can degrade the image quality if the data is not corrected for attenuation caused by the table and coils.

In PET imaging, an attenuation map of the patient is generated and used to correct the PET data. When performing PET/CT, a CT image is often used to generate the patient attenuation map. The attenuation for CT, which has an energy of 40-120 keV, is not the same as the attenuation for PET, which has energy of 511 keV. However, over the years, the relationship between CT attenuation values and PET attenuation values for human tissue has become well-known. Such algorithms are described in C. Bai et al., "A Generalized Model for the conversion from CT numbers to linear attenuation coefficients," IEEE Trans. Nucl. Sci., Vol. 50, No. 5, Oct. 2003.

The transformation described by C. Bai et al. is effective for materials generally found in human body, but it is ineffective in the case of table and coils due to the presence of metals and materials such as urethane, poly-vinyl chloride (PVC), etc. The LAC values of the materials used in the table and coils are not commonly found in the literature (See, e.g., J. H. Hubbell, "Photon cross sections, attenuation coefficients, and energy absorption coefficients from 10 keV to 100 GeV," National Bureau of Standards, August 1969).

There is an unmet need in the art for systems and methods that facilitate correcting for attenuation in an MR image caused by RF coils, accessories (e.g., a nurse call button device, headphones, etc.), a patient support table, and the like, thereby overcoming the deficiencies noted above.

In accordance with one aspect, a system that generates an attenuation correction (AC) map template for correcting attenuation in a nuclear image caused by accessories in a nuclear scanner field of view during a nuclear scan includes a processor that generates an AC map template of an accessory from transmission data acquired during a nuclear scan of the accessory, stores the AC map template to a memory; and iteratively generates a unique AC map template for each of a plurality of different accessories, the templates being stored in a template library in the memory for recall and use by an operator.

In accordance with another aspect, a method of generating an attenuation correction (AC) map template for an magnetic resonance (MR) coil includes attaching a plurality of fiducial markers to an MR coil, acquiring scan data of the MR coil and fiducial markers, generating an AC map template of the MR coil with the fiducial markers, and storing the AC map template. The method further includes iteratively generating a unique AC map template for each of a plurality of different accessories, the AC map templates being stored in a template library in a memory for recall and use by an operator.

In accordance with another aspect, a method of generating an attenuation corrected nuclear image includes positioning a selected MR coil about a patient, acquiring MR scan data of the patient and the coil, and reconstructing the MR scan data into an MR patient image. The method further includes retrieving an AC map template corresponding to the selected MR coil from a library, generating a patient-specific attenuation correction (AC) map, and combining the AC map template and the patient-specific AC map to generate a final AC map. Additionally, the method includes acquiring nuclear scan data of the patient and the selected MR coil, correcting attenuation in the nuclear scan data using the final AC map, and reconstructing the attenuation corrected nuclear scan data into a nuclear image.

In accordance with another aspect, a library of attenuation correction (AC) map templates is stored to a data storage medium, and includes at least one pre-generated AC map template for each of a plurality of magnetic resonance (MR) coils. The at least one AC map template is retrieved from the library upon entry of a coil identification code that identifies an MR coil for which a template is desired. The at least one AC map template is generated from transmission data acquired during a nuclear scan of each MR coil in the plurality of coils.

According to another aspect, a method of adjusting a patient attenuation correction (AC) map for correcting attenuation in nuclear scan data includes receiving coil identification information that identifies a coil for which an AC map template is desired, retrieving the identified AC map template from a template library stored in a memory, and adapting the AC map template to conform to a contour of a patient in a patient image. The method further includes inserting the adapted AC map template into a patient-specific attenuation correction (AC) map to generate a final AC map, and correcting attenuation when reconstructing nuclear scan data of a patient to generate an attenuation-corrected nuclear image of the patient.

One advantage is that attenuation caused by MR coils is made correctable.

Another advantage of one embodiment resides in generating and morphing an attenuation correction (AC) map template of an MR coil to a patient body contour.

Still further advantages of the subject innovation will be appreciated by those of ordinary skill in the art upon reading and understand the following detailed description.

The innovation may take form in various components and arrangements of components, and in various steps and arrangements of steps. The drawings are only for purposes of illustrating various aspects and are not to be construed as limiting the invention.

In accordance with various features presented herein, systems and methods are described that facilitate generating an attenuation map of the table and coils using a transmission scan on a PET system with built-in transmission source, such as is described by J. S. Karp et al., in "Singles transmission in volume-imaging PET with a Cs-137 source," Phys. Med. Biol., 40, pp 929-944, 1995, which is incorporated by reference in its entirety herein. The transmission scan provides the attenuation coefficient for the material in the table and coils at an energy very similar to the PET gamma energy (511 keV). In this manner, PET image quality is significantly improved, and generation of the attenuation map of the table and coils is improved.

The herein-described systems and methods solve the problem of generating an attenuation map for the patient table and MR coils, which is difficult to generate using a CT scan because CT energy ranges from 40-120 keV while PET attenuation is measured at 511 keV. Classical conversion procedures are not applicable to materials employed in the MR table and coils. For instance, the metal causes metal artifacts in the CT image, and other issues such as scatter and beam hardening prevent derivation of an accurate CT attenuation map of the table and coils. Accordingly, using a transmission scan as described herein facilitates providing an attenuation map of the coils at either 511 keV (using Ge-68) or 662 keV (using Cs-137), which is very close to the 511 keV PET attenuation map. Hence this approach can significantly improve the image quality of PET images reconstructed using the herein-described enhanced MR attenuation map. The described systems and methods also enable the use of MR coils inside a PET gantry, leading to generation of diagnostic-quality MR image data correctly registered with the PET image.

The template libraries generated by the described systems and methods can be stored to a data storage medium or memory for distribution to users of medical scanners or imaging devices in which the templates are employed to enhance attenuation correction. For instance, a template library can be stored to a portable storage medium that is sent to a user, or may be downloaded from a central server to the user's network (e.g., in a hospital or the like). In another embodiment, the template library (or a single template, etc.) is provided to a user upon purchase of a coil for which a template exists in the library. That is, when a user purchases a specific coil, an AC map template therefor is also provided to the user. The user then adapts the coil according to the methods described herein and inserts the adapted template into a patient-specific AC map to generate a final AC map that is used to correct for attenuation when reconstructing nuclear scan data into a nuclear image.

Figure 1:
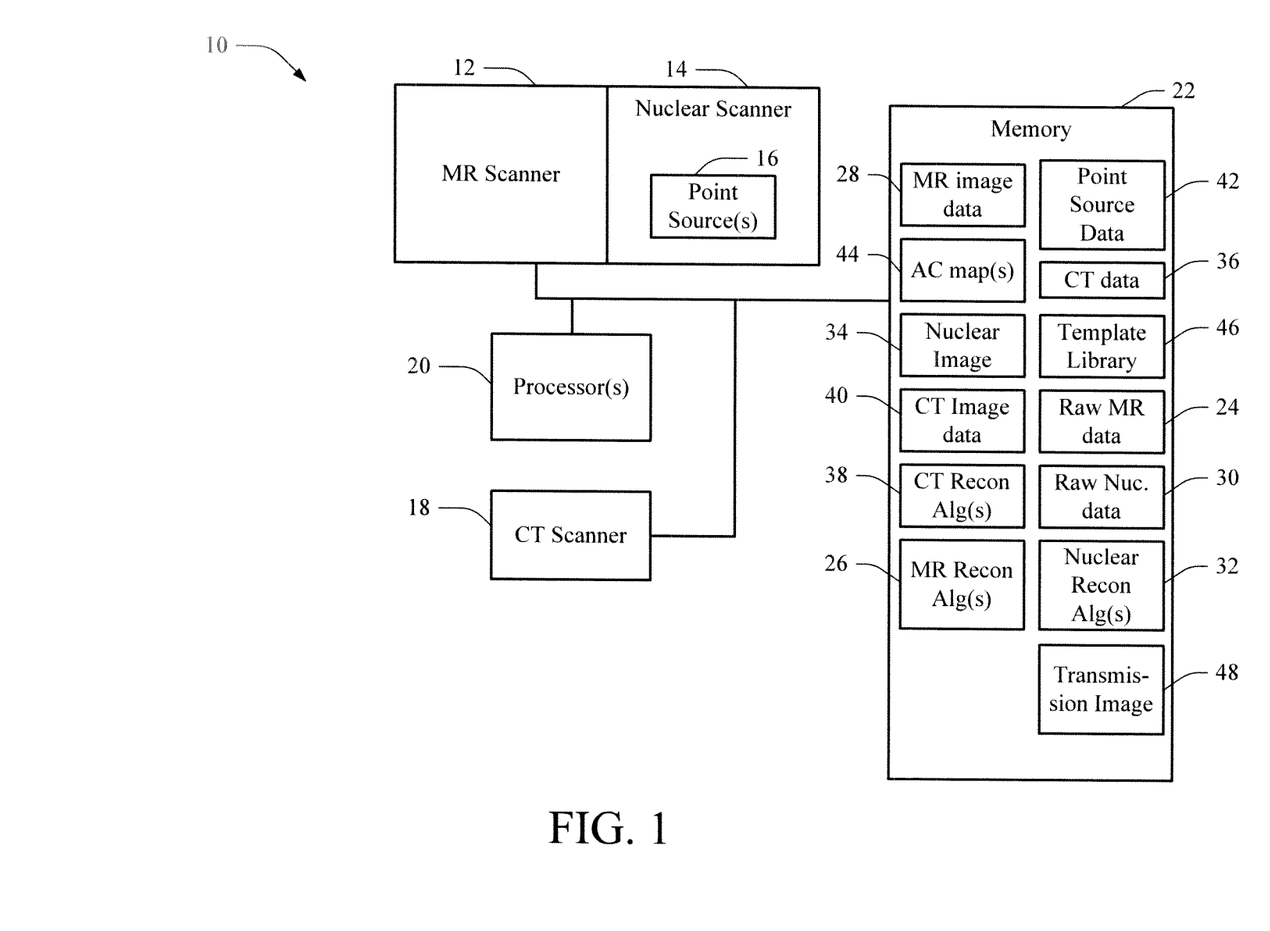
FIG. 1 illustrates a system that facilitates generating attenuation map templates for flexible or rigid MR coils using transmission scan information, with or without using CT scan information.

FIG. 1 illustrates a system 10 that facilitates generating attenuation map templates for flexible or rigid MR coils using transmission scan information, with or without using CT scan information. The system 10 includes an MR scanner 12 and a nuclear scanner 14, such as a PET scanner, a single photon emission computed tomography (SPECT) scanner, variants of the foregoing, etc. A point source 16 is positioned in the nuclear scanner to provide transmission data that is used to form one or more attenuation map templates. Optionally, a CT scanner 18 is included in the system 10 to provide additional data regarding attenuation-causing items, such as the MR coils and/or patient support table.

One or more processors 20 execute computer-executable instructions and/or algorithms stored in a data storage medium or memory 22, to perform the various functions described herein. The memory 22 stores raw MR data 24 as well as one or more MR reconstruction algorithms 26 that are executed by the processor to reconstruct the raw MR data (e.g., acquired during an MR scan) into MR image data 28. Raw nuclear data 30 is acquired during a nuclear scan and stored in the memory. The MR and nuclear data in one embodiment are acquired concurrently, and in another embodiment they are acquired sequentially. The processor executes one or more nuclear reconstruction algorithms 32 to reconstruct the raw nuclear data into nuclear image data 34. Additionally, the memory stores acquired CT image data 36, and the processor executes one or more CT reconstruction algorithms 38 when reconstructing the raw CT data into CT image data 40. It will be appreciated that the processor(s) 20 may be a single processor, or may comprise a plurality of dedicated processor (e.g., data processors, reconstruction processors, etc.).

The memory 22 additionally stores point source data 42, also called transmission data herein, generated during a nuclear scan in which the point source 16 is employed. One or more subject (or patient) specific attenuation correction (AC) maps 44 are stored in the memory, and are employed when reconstructing the nuclear image to correct for attenuation. In one embodiment, the AC maps of the subject are generated at least in part from the MR image data 28.

A template library 46 stores one or more accessory AC map templates, which are generated using transmission data 42 for MR coils, the patient table, other accessories, and the like that may be introduced into a field of view of the nuclear scanner. The accessory templates are combined with the subject-specific AC map(s) 44.

In one embodiment, the subject specific AC map 44 is a PET AC map (e.g., for correcting attenuation in a PET image), and is derived using MR image data. For example, an MR image of a patient is produced using a whole-body MR coil. The patient's body outline and other internal organ boundaries are established, and the MR image is segmented by the processor 20. PET radiation attenuation values of lung, soft-tissue, bone, etc. are assigned to create an attenuation map for the patient. A high-resolution MR image of the same patient is produced using the RF coils. Nuclear image data of the same patient is produced with the MR coils in the field-of-view, to acquire raw nuclear scan data 30. A pre-generated AC template of the coil, which was created before the acquisition, is retrieved from the template library 46, and is used for all scan data acquisitions using that coil. The template is combined with the subject-specific AC map 44 to generate full or combined AC map. The raw PET data 30 is reconstructed using the full or combined AC map.

In another embodiment, the subject specific AC map 44 is a SPECT AC map (e.g., for correcting attenuation in a SPECT image), and is derived using MR image data. For example, an MR image of a patient is produced using a whole-body MR coil. The patient's body outline and other internal organ boundaries are established, and the MR image is segmented by the processor 20. SPECT radiation attenuation values of lung, soft-tissue, bone, etc. are assigned to create an attenuation map for the patient. A high-resolution MR image of the same patient is produced using the RF coils. Nuclear image data of the same patient is produced with the MR coils in the field-of-view, to acquire raw nuclear scan data 30. A pre-generated AC template of the coil, which was created before the acquisition, is retrieved from the template library 46, and is used for all scan data acquisitions using that coil. The template is combined with the subject-specific AC map 44 to generate full or combined AC map. The raw SPECT data 30 is reconstructed using the full or combined AC map.

With regard to template generation, the patient support table and/or coil or other accessory is imaged inside the nuclear scanner 14 (e.g., PET or SPECT) with the transmission source 16 (e.g., Ge-68 or Cs-137). A transmission image 48 is reconstructed using the known algorithms and may be used as the accessory template directly.

Figure 2:
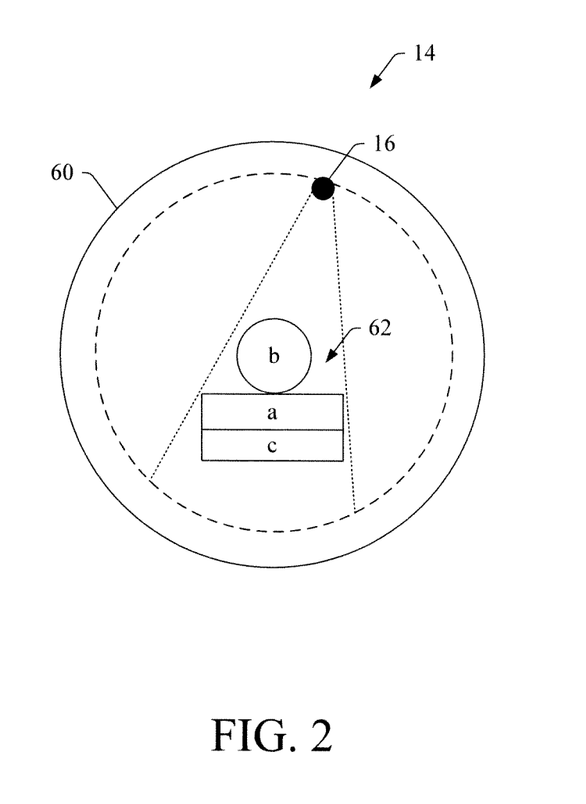
FIG. 2 illustrates the nuclear scanner (e.g., a PET scanner) with the point source mounted on a rotatable gantry that rotates about coil apparatus, such as may be employed to perform a transmission scan of the coil apparatus.

Alternatively, the template can be generated in the following manner. A global histogram of the transmission image is generated, and the segments of the coil or other accessory are identified. The average linear attenuation coefficient (LAC) value is determined from the distribution of the histogram. The coil or other accessory is imaged using a high resolution CT scan, and the CT image is segmented and assigned the computed LAC values determined from the distribution of the histogram to create the template for the coil. FIG. 2 illustrates the nuclear scanner 14 (e.g., a PET scanner, a SPECT scanner, etc.) with the point source 16 mounted on a rotatable gantry 60 that rotates about a coil or other accessory 62, such as may be employed to perform a transmission scan of the coil or other accessory. The accessory in the example includes three components, labeled a, b, and c. In one embodiment, component a is a local RF coil, component b is a planar RF coil, and component c is a patient support table. The linear attenuation coefficient (LAC) values of the three components are estimated from a transmission map generated during the transmission scan, and assigned three respective LAC values: $\mu_a$, $\mu_b$, $\mu_c$. These values are used for creating a segmented attenuation map of the accessory 62 and can be pre-stored in the library and used for all reconstructions involving the accessory. The segmentation can be performed on a high-resolution CT image of the coil.

Transmission source 16 (e.g., Ge-68 or Cs-137) measurements are employed to generate the attenuation map of the MR table, coils, and other accessories. Typically, transmission images have a common drawback of low statistics and resolution. However, high statistics can be obtained by executing a long transmission scan, since the attenuation map of the table and coils needs to be created only once and can be used for all PET (or SPECT) reconstruction. An advantage of this approach is that the accurate determination of the attenuation values of the materials of the table and coils at 511 keV is possible, which is difficult using a CT scan. It has been observed from studies using different MR coils that PET (or SPECT) images reconstructed with the attenuation map of the coils obtained using a CT scan typically may be subject to overcorrection for attenuation. This drawback is overcome by the described systems and methods.

Figure 3:
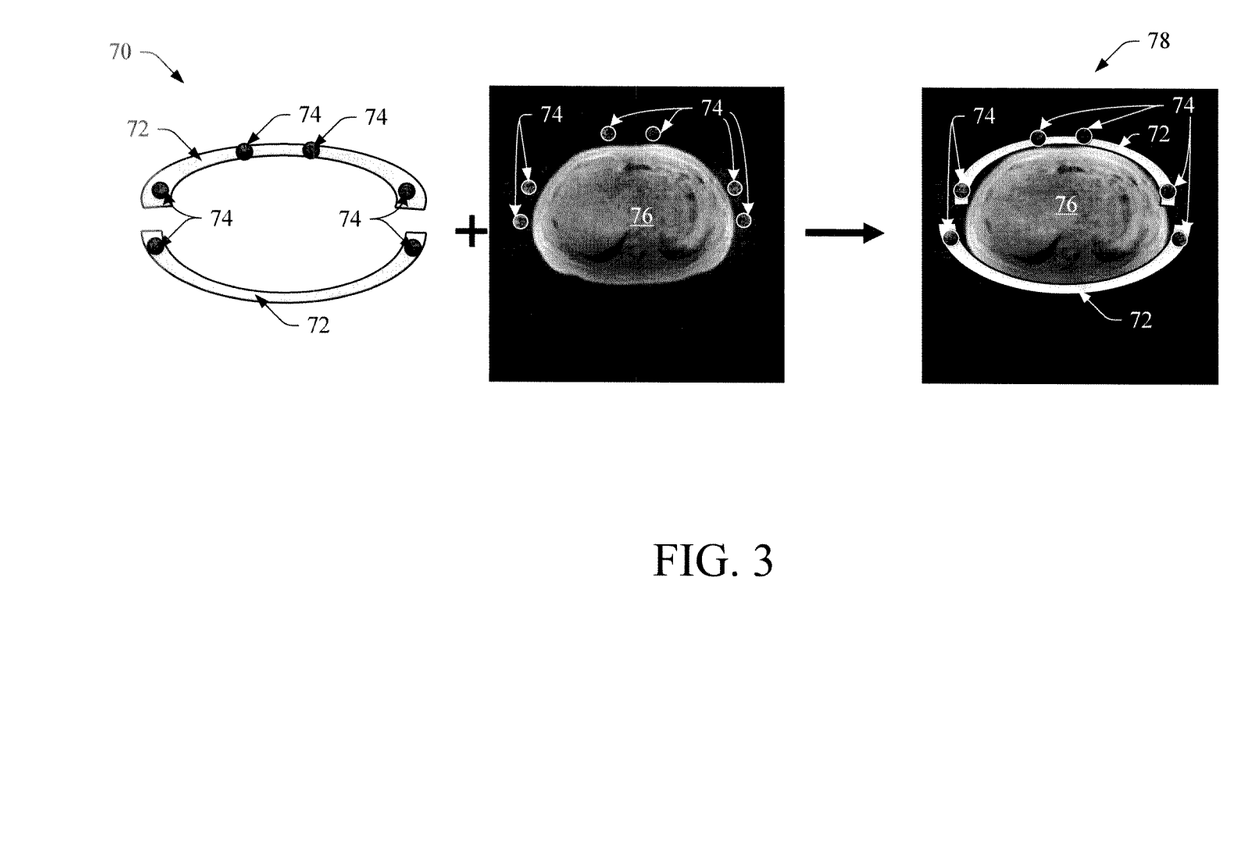
FIG. 3 illustrates an AC map template of flexible MR coils, generated using CT or transmission data of the MR coils with a plurality of fiducial markers positioned thereon, which facilitate morphing the AC map template to an MR image of a patient to generate a final (e.g., transformed) patient AC map for the coils adjusted to fit the patient.

FIG. 3 illustrates an AC map template 70 of flexible MR coils 72, generated using CT or transmission data of the flexible MR coils. A plurality of MR imagable fiducial markers 74 are positioned thereon, to facilitate morphing the AC map template 70 to a configuration for imaging the patient, to match a surface shape of the patient as seen in MR image 76. For instance, AC map templates are pre-generated for each of a plurality of MR coils. When a particular MR coil is to be employed on a patient, its AC map template is selected and morphed into registration with the MR fiducial markers in an MR scan of the patient. The shape of the coils is thereby adjusted to conform to the contours of the patient.

According to one embodiment, the fiducial markers 74 are attached to the coils 72, which are then scanned using a PET (or SPECT) scanner (e.g., nuclear scanner 14 of FIG. 1 or 2) with a transmission source or a CT scanner 18 (FIG. 1) to generate the AC map template wherein the fiducial markers are visible and identified. In a subsequent PET (or SPECT) and MR study, the coil is scanned with the patient using an MR imager (FIG. 1), where the fiducial markers are also visible in the MR image 76 (although the coils are not). The fiducial markers in the MR image 76 are registered with those in the AC map template 70 (e.g., using elastic image registration, or the like) to generate the final patient AC map.

Fiducial markers are thus attached to flexible coils, the MR image shows the locations of the markers, and the AC map template 70 of the flexible coils 72 is registered with the MR image 76 using the fiducial markers and is then combined into the patient-specific attenuation map. In this manner, attenuation correction is facilitated for flexible MR coils and/or non-rigid portions of an otherwise rigid MR coil or other accessories that may be placed in the imaging region.

In one embodiment, the AC map template is registered and aligned in axial and lateral directions, with the vertical direction being known from the table height. The only remaining variable is the shape of the flexible coil on the body. This variable is ascertained by registering the fiducial markers to elastically transform the coil template to the body contour.

Figure 4:
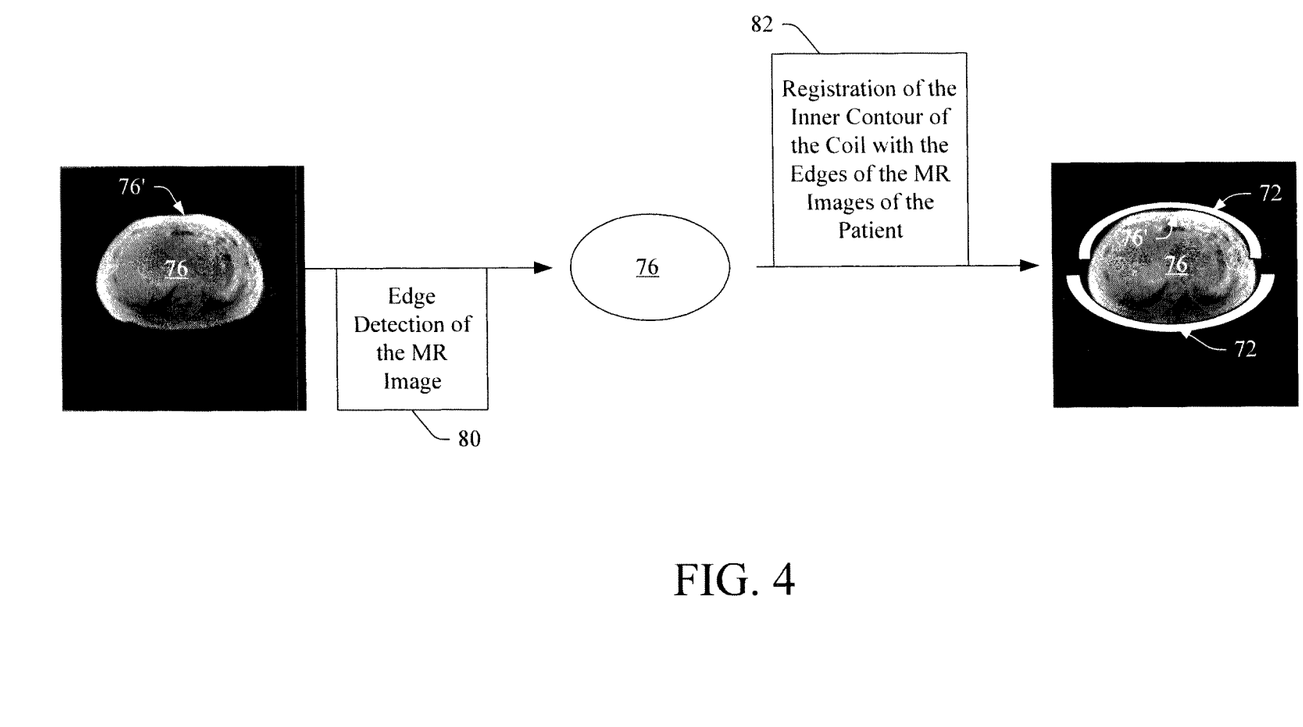
FIG. 4 illustrates another example of a manner in which the MR coil AC map template is fitted to the patient MR image, in accordance with various aspects described herein.

FIG. 4 illustrates another example of a manner in which the MR coil AC map template 72 is fitted to the patient, in accordance with various aspects described herein. For example, at 80, an edge detection technique or algorithm is performed on the MR image 76 of a patient or volume of interest to define a surface 76' of the patient. The inner surface of the flexible coil is matched or transformed into conforming to the body contour 76'.

In one embodiment, the coil is scanned using a CT or PET (or SPECT) system with a transmission source to generate the AC map template 72. Later, an MR scan is performed of the patient with the MR coil positioned thereabout. The patient body contour is identified, and assumed to be the same as the inner surface of the coil using the edge detection technique. The inner surface of the AC map template is morphed or conformed to the patient body contour, and the morphed template is inserted into the final patient attenuation map.

Figure 5:
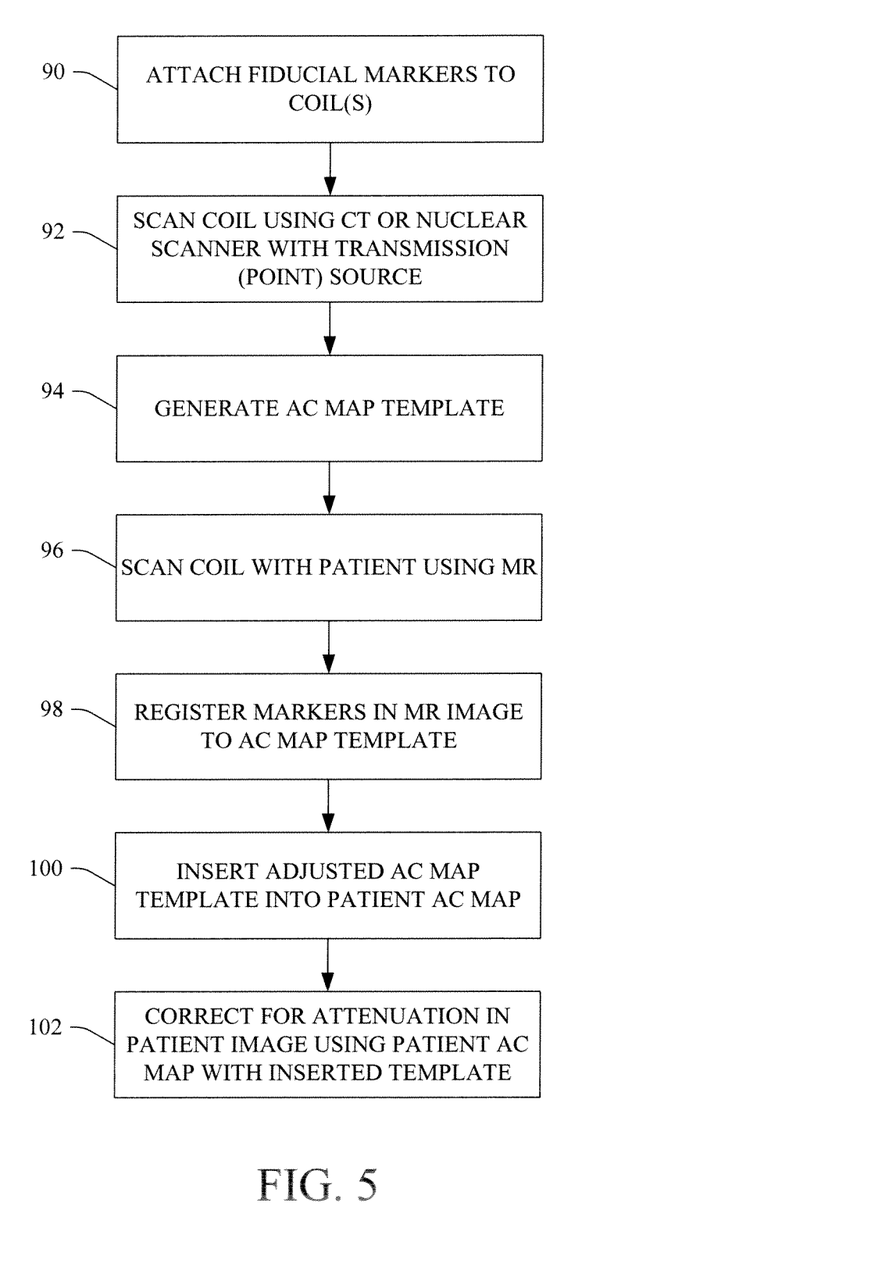
FIG. 5 illustrates a method for conforming an AC map template, which is generated using CT or transmission data, to an MR image of a patient to generate an MR-based patient AC map for correcting attenuation due to flexible MR coils or portions thereof, a patient support, or other accessories, in a nuclear image (e.g., PET or SPECT).

FIG. 5 illustrates a method for generating and conforming a deformable AC map template, which is generated using CT or transmission data, to an MR image of a patient to generate an MR-based patient AC map for correcting attenuation due to flexible MR coils or portions thereof, a patient support, or other accessories, in a nuclear image (e.g., PET or SPECT). The MR-based patient AC map is generated using one or more known techniques.

At 90, fiducial markers are attached to an MR coil or other accessory. At 92, the MR coil is scanned using CT, a nuclear scanner (PET or SPECT) with a transmission source (e.g., a point source), or the like. From the CT or transmission data, an AC map template is generated for the coil, at 94. It will be appreciated that steps 90, 92, and 94 may be executed well in advance of application of the AC map template to a patient MR image. For instance, the manufacturer of each type and/or size of MR coil can scan the coil in advance, and generate an AC map template that is sold with the coil. When a patient requires an MR and nuclear scan, the AC map template is recalled from the library for use in correcting attenuation caused by the MR coil during the nuclear scan.

At 96, the coil, with fiducial markers attached, is placed about the patient and an MR scan is performed. At 98, the fiducial markers in the AC map template are registered to the fiducial markers in the MR image of the patient, which causes the AC map template to conform or morph to the patient image. Registration may be performed manually by a technician or operator, semi-automatically, or automatically using a computer-executable algorithm or technique (e.g., stored in a memory and executed by a processor).

At 100, the morphed AC map template is inserted (e.g., overlaid, etc.) into the patient-specific AC map for correcting attenuation in nuclear image data, to generate a final patient AC map. At 102, the final AC map is employed to correct for attenuation in nuclear scan data when reconstructing the acquired nuclear scan data into a nuclear image of the patient.

Figure 6:
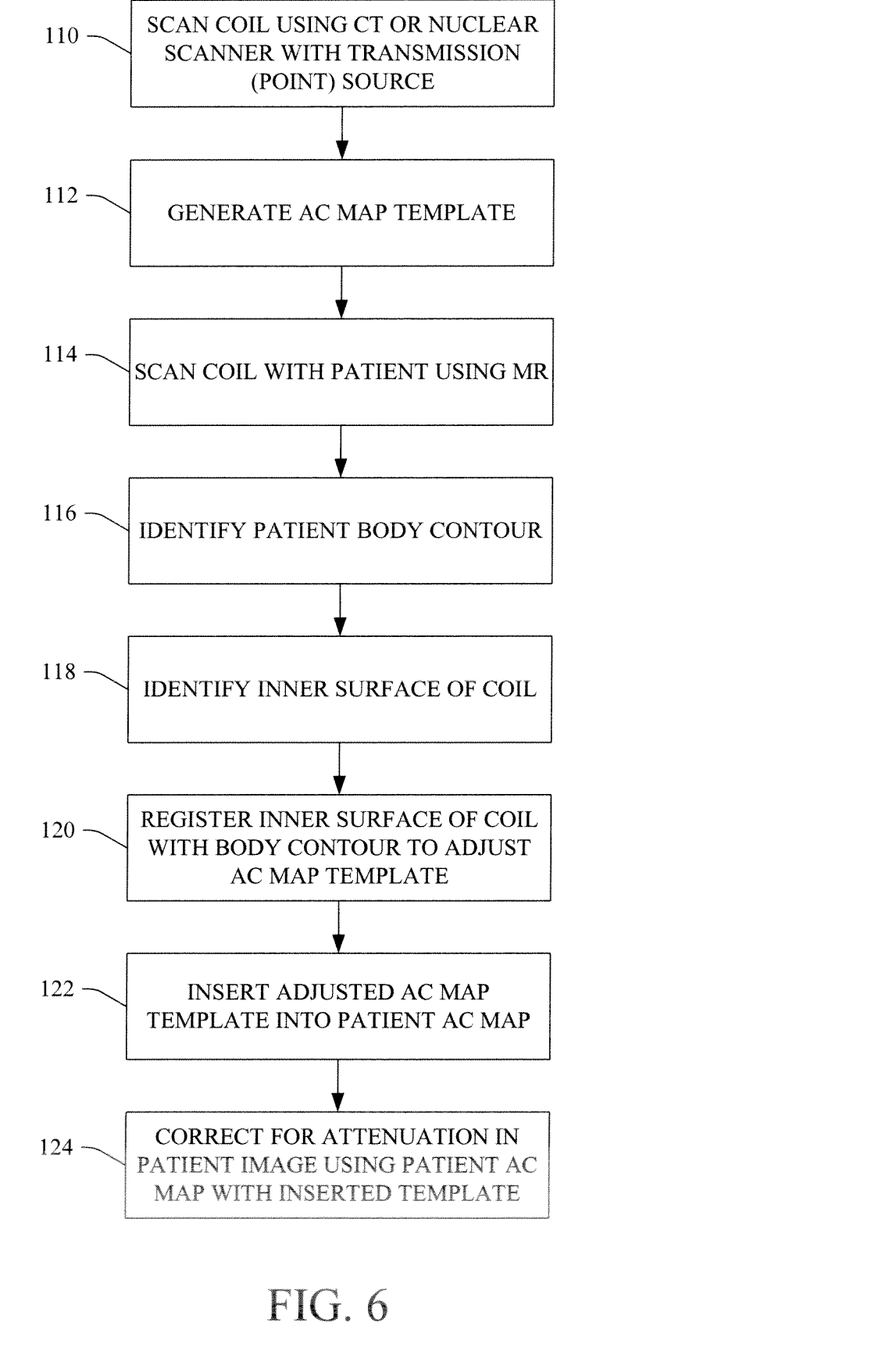
FIG. 6 illustrates a method of conforming an AC map template, which is generated using CT or transmission data, to an MR image of a patient to generate an MR-based patient AC map for correcting attenuation in a nuclear image (e.g., PET or SPECT) without employing fiducial markers.

FIG. 6 illustrates a method of conforming an AC map template, which is generated using CT or transmission data, to an MR image of a patient to generate an MR-based patient AC map for correcting attenuation in a nuclear image (e.g., PET or SPECT) without employing fiducial markers. At 110, a flexible MR coil is scanned using a CT scanner, or a nuclear scanner (PET or SPECT) with a transmission source (e.g., a point source). From the CT or transmission data, an AC map template is generated for the coil, at 112. It will be appreciated that steps 110 and 112 may be executed well in advance of application of the AC map template to a patient MR image, as described with regard to steps 90, 92, and 94 of FIG. 5.

At 114, the coil is placed about the patient and an MR scan is performed. At 116, a patient body contour is identified in the MR image. At 118, an inner surface of the coil is identified in AC map template. Detection of the body contour and/or the inner surface of the coil can be performed, for instance, using an edge-detection technique, such as is known in the art. At 120, the inner surface of the coil is registered with the body contour to adjust or morph the template to the patient image. At 122, the morphed AC map template is inserted (e.g., overlaid, etc.) into an AC map for correcting attenuation in a nuclear image, to generate a final patient AC map. At 124, the final AC map is employed to correct for attenuation in nuclear scan data when reconstructing the acquired nuclear scan data into a nuclear image of the patient.

Figure 7:
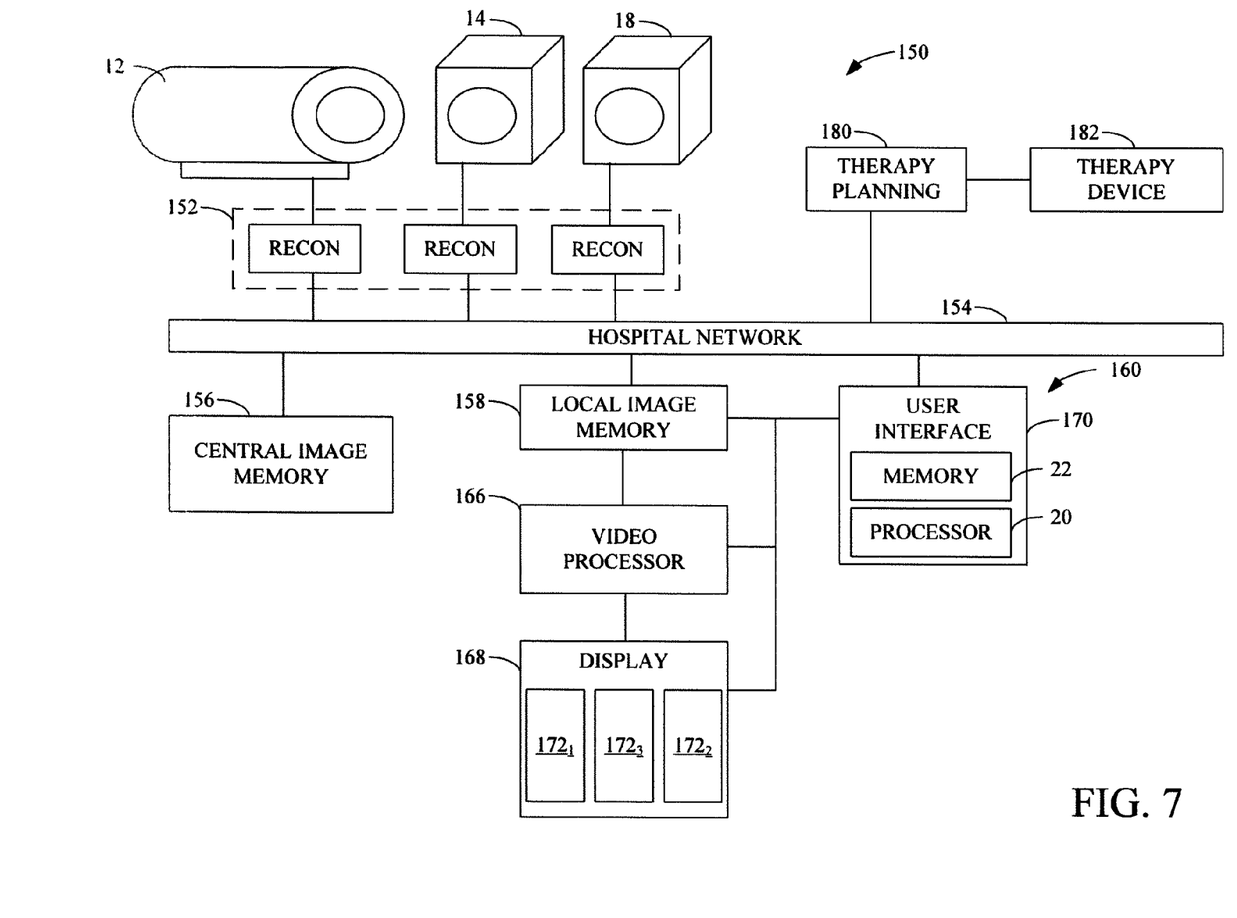
FIG. 7 illustrates an exemplary hospital system that includes a plurality of imaging devices, such as an MR imaging device, a nuclear scanner (e.g., PET or SPECT), a CT scanner, or the like, which generate imaging data that are reconstructed by individual or shared reconstruction processors to generate 3D image representations.

With reference to FIG. 7, an exemplary hospital system 150 may include a plurality of imaging devices, such as an MR imaging device 12, a nuclear scanner 14 (e.g., PET or SPECT), a CT scanner 18, or the like, which generate imaging data that are reconstructed by individual or shared reconstruction processors 152 to generate 3D image representations. The image representations are communicated over a network 154 to a central memory 156 or a local memory 158.

At a station 160 connected with the network, an operator uses user interface 170 to move a selected 3D AC map template to or between the central memory 156 and the local memory 158. A video processor 166 displays the selected AC map template for a selected MR coil in a first viewport $172_1$, of a display 168. A patient MR image (e.g., of the patient and MR coil) is displayed in a second viewport $172_2$. A third view port $172_3$ can display an overlay of the AC map template and the MR image. For example, a user can be permitted to register fiducial markers in the coil AC map template to corresponding markers in the MR image. For instance, the operator, through the interface 170, selects the fiducial markers in the template (e.g., using a mouse, stylus, or other suitable user input device) that correspond to fiducial markers in the MR image. Alternately, the fiducial markers can be aligned automatically by a program executed by the processors 20 and/or 166, which is stored in the memory 22. The processor 20 (FIG. 1) in the user interface 170 then performs a warping or morphing algorithm to conform the shape of the coil in the AC map template to the shape of the patient in the MR image using the aligned fiducial markers.

In another embodiment, the processor 20 executes an edge detection algorithm to identify contours of the patient in the MR image, and aligns an interior surface of the coil in the AC map template to the identified contour.

The morphed template is inserted into an MR attenuation map generated from MR data acquired during an MR scan of the patient to generate a refined attenuation map that is then used to reconstruct an attenuation-corrected nuclear image, which may be used in other applications. For instance, a therapy planning station 180 can use the attenuation-corrected PET image to plan a therapy session. Once planned to the satisfaction of the operator, the planned therapy can, where appropriate to an automated procedure, be transferred to a therapy device 182 that implements the planned session. Other stations may use the attenuation-corrected PET image in various other planning processes.

In another embodiment, the overlay displayed in viewport $172_3$ is adjustable to weight the coil AC map template relative to the MR image, or vice versa. For instance a slider bar or knob (not shown), which may be mechanical or presented on the display 168 and manipulated with an input device, may be adjusted to vary the weight of the MR image or the AC map template. In one example, an operator can adjust the image in viewport $172_3$ from purely MR image data (shown in viewport $172_2$), through multiple and/or continuous combinations of MR and AC map template image data, to purely AC map template image data (shown in viewport $172_1$). For instance, a ratio of MR image data to AC map template image data can be discretely or continuously adjusted from 0:1 to 1:0. As another option, the MR image can be displayed in grayscale and the AC map template image can be colorized, or vice versa. Fiducial markers in the MR image help relate the Ac map template image to the subject.

The described systems and methods can be used, for instance, in a hybrid imaging system with the MR table and coils in the field-of-view of nuclear detectors (e.g., PET or SPECT).

Templates are stored in the template library 46 (FIG. 1), which, in one embodiment, is stored to a portable data storage medium or memory (e.g., a CD, flash drive, memory stick, memory card, or other suitable portable storage medium. The stored library is then provided to a purchaser or operator for use in correcting attenuation in nuclear images.

In another embodiment, the template library is stored on a memory at a server and is downloadable by a user or purchaser to a client-side memory (e.g., the central memory 156) for use in correcting attenuation in a nuclear image.

Once a user has downloaded and/or installed the template library to the central memory 156, the library can be accessed via the network to facilitate final AC map generation, attenuation correction, and the like as described herein. For instance, an operator can input a coil identification code using the user interface 170, and the processor 20 retrieves a corresponding coil template from the central memory 156, which is then used to generate the final AC map for attenuation correction when reconstructing a nuclear image as described herein. According to this example, multiple workstations or user interfaces can access the template library as need for specific patients or imaging sessions that employ coils for which templates are provided in the library.

In another embodiment, template libraries are provided to users as upgrade packages for existing or previously purchased scanners and/or imaging devices, via downloads, and/or upon purchase of one or more coils having for which a template has been pre-generated and stored in the library.

Figure 8:
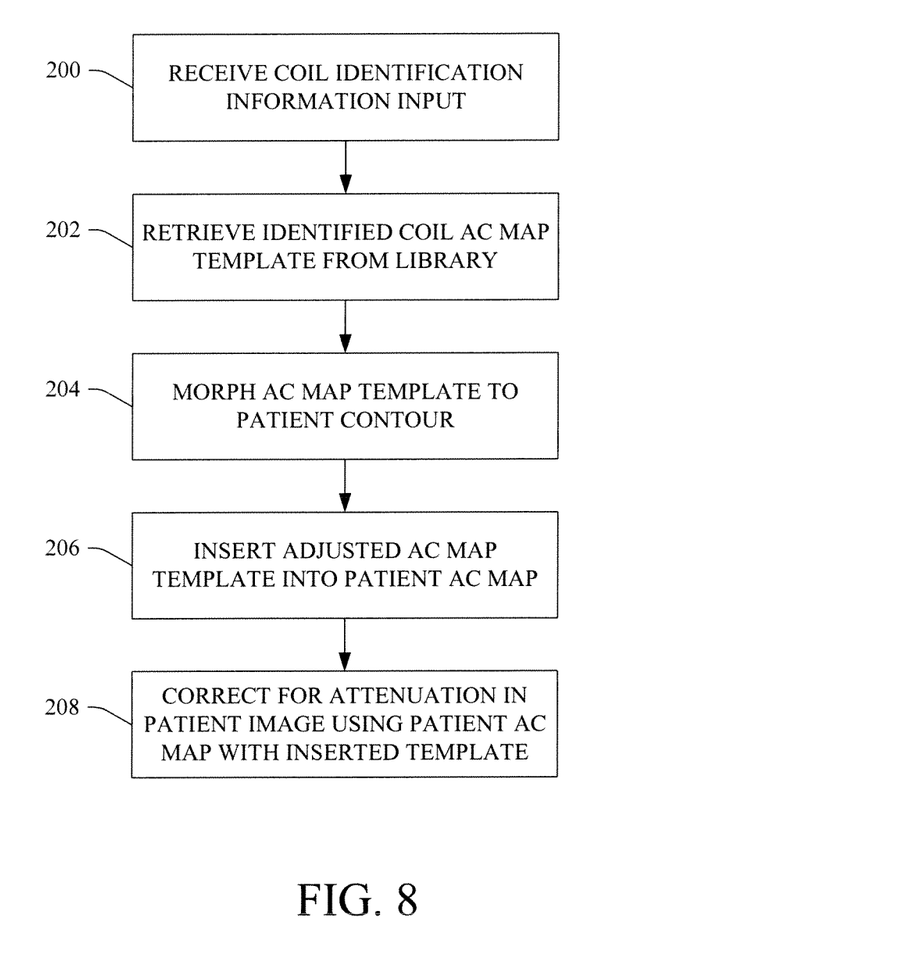
FIG. 8 illustrates a method of retrieving a coil template from a template library and enhancing an AC map for attenuation correction when reconstructing a nuclear image.

FIG. 8 illustrates a method of retrieving a coil AC map template from a template library and enhancing an AC map for attenuation correction when reconstructing a nuclear image. At 200, coil identification information is received as input. The coil identification information may be a coil identification code, where each coil has a unique identification code (numerical, alphabetical, alphanumerical, etc.), which is input by a user to identify the coil for which a template is desired. IN another example, the coil identification information is input by a user by selecting an icon or picture of a coil on a user interface (e.g., using a mouse, keypad, directional arrows, stylus, etc.). Once the coil identification information is received, a template for the identified coil is retrieved from a template library, at 202. At 204, the coil template is morphed to conform to a patient contour (e.g., using the fiducial marker technique or the edge-detection technique described with regard to FIGS. 5 and 6, respectively). At 206, the adjusted AC map template is inserted into a patient AC map to generate a final AC map. At 208, attenuation correction is performed using the final AC map during reconstruction of nuclear scan data into a nuclear image (e.g., PET or SPECT).

The innovation has been described with reference to several embodiments. Modifications and alterations may occur to others upon reading and understanding the preceding detailed description. It is intended that the innovation be construed as including all such modifications and alterations insofar as they come within the scope of the appended claims or the equivalents thereof.

Having thus described the preferred embodiments, the invention is now claimed to be:

1. A system that generates an attenuation correction (AC) map template for correcting attenuation in a nuclear image caused by accessories in a nuclear scanner field of view during a nuclear scan, including:
   a processor that:
   generates an AC map template of an accessory from transmission data acquired during a nuclear scan of the accessory;
   receives scan data of the accessory from a nuclear scanner with a transmission source;
   determines an average linear attenuation coefficient (LAC) value from a distribution of a histogram of transmission data values; and
   assigns the average LAC value to the accessory when generating the AC map template;
   stores the AC map template to a memory; and
   iteratively generates a unique AC map template for each of a plurality of different accessories, the templates being stored in a template library in the memory for recall and use by an operator.

2. The system according to claim 1, wherein the accessories include an MR coil, and further including:
   an MR imaging device that images a patient with the MR coil positioned in the field of view of the MR imaging device;
   wherein the processor:
   loads stored AC map templates into a library;
   retrieves an AC map template for a selected MR coil from the library; inserts the AC map template into an MR-based AC map to generate a final AC map;
   corrects attenuation caused by the MR coil in nuclear image data of the patient in which the MR coil present in the field of view of the nuclear scanner during a scan of the patient; and
   reconstructs the attenuation-corrected nuclear image data into an image.

3. The system according to claim 2, wherein the processor adjusts the AC map template to conform to a contour of the patient.

4. The system according to claim 3, wherein the processor executes, and the memory stores, a set of computer-executable instructions for performing an edge detection technique that identifies the contour of the patient, and wherein the processor adjusts the shape of the AC map template to conform to the contour.

5. The system according to claim 3, further comprising:
   fiducial markers attached to the MR coil, the locations of the fiducial markers being identified in the AC map template;
   wherein MR data acquired during the MR scan is reconstructed to generate an MR patient image in which the fiducial markers are visible.

6. The system according to claim 1, wherein the nuclear scanner is at least one of a positron emission tomography (PET) scanner and a single photon emission computed tomography (SPECT) scanner.

7. The system according to claim 1, wherein the transmission source is at least one of a Germanium-68 (Ge-68) point source and a Cesium-137 (Cs-137) point source.

8. The system according to claim 1, wherein the accessory is an MR coil, and wherein the processor determines at least one linear attenuation coefficient (LAC) value for the coil, and generates the AC map template for the coil using the at least one LAC value.

9. A method of generating an attenuation correction (AC) map template for an magnetic resonance (MR) coil, including:
   attaching a plurality of fiducial markers to an MR coil;
   acquiring scan data of the MR coil and fiducial markers;
   generating an AC map template of the MR coil with the fiducial markers;
   acquiring MR scan data of the patient and the coil;
   reconstructing the MR scan data into an MR patient image;
   registering the fiducial markers in the AC map template to the fiducial markers in the MR patient image to conform the AC map template to a body contour in the MR patient image;
   storing the AC map template; and
   iteratively generating a unique AC map template for each of a plurality of different accessories, the AC map templates being stored in a template library in a memory for recall and use by an operator.

10. The method according to claim 9, further including:
    positioning the MR coil about a patient;
    inserting the AC map template into an MR-based AC map of the patient to generate a final AC map; and
    employing the final AC map to correct for attenuation caused by the MR coil in a nuclear image of the patient.

11. The method according to claim 10, wherein the MR coil is a flexible MR coil.

12. The method according to claim 9, wherein the scan data of the MR coil is acquired using a CT scanner; and further including:
    segmenting a CT image of the MR coil;
    acquiring scan data of the MR coil using a positron emission tomography (PET) scanner with a transmission source;
    generating a global histogram of the transmission image; and
    fitting histogram values to the segmented CT image to generate the AC map template.

13. A non-transitory computer-readable medium that carries software for controlling a processor to perform the method of claim 9.

14. A method of generating an attenuation corrected nuclear image, including:
    positioning a selected MR coil about a patient;
    acquiring MR scan data of the patient and the coil;
    reconstructing the MR scan data into an MR patient image;
    determining an average linear attenuation coefficient (LAC) value from a distribution of a histogram of transmission data values for the MR coil acquired using a nuclear scanner;
    retrieving an AC map template corresponding to the selected MR coil from a library;
    generating a patient-specific attenuation correction (AC) map;
    combining the AC map template and the patient-specific AC map to generate a final AC map;
    acquiring nuclear scan data of the patient and the selected MR coil;
    correcting attenuation in the nuclear scan data using the final AC map; and
    reconstructing the attenuation corrected nuclear scan data into a nuclear image.

15. The method according to claim 14, further including:
    acquiring scan data of the MR coil using a CT scanner;
    segmenting a CT image of the MR coil;
    wherein the nuclear scanner is a positron emission tomography (PET) scanner with a transmission source;
    generating the histogram of the transmission data values; and
    fitting histogram values to the segmented CT image to generate the AC map template.

16. The method according to claim 14, further including:
    assigning the average LAC value to the MR coil to generate the AC map template.

17. The method according to claim 16, further including performing an edge detection technique that identifies a contour of the patient, and adjusting the shape of the AC map template to conform to the contour.

18. An imaging system that includes one or more processors programmed to perform the method of claim 14.

19. A library of attenuation correction (AC) map templates stored in a memory, including:
    at least one pre-generated AC map template for each of a plurality of magnetic resonance (MR) coils;
    wherein the at least one AC map template is retrieved from the library upon entry of a coil identification code that identifies an MR coil for which a template is desired;
    wherein the at least one AC map template is generated from transmission data acquired during a nuclear scan of each MR coil in the plurality of coils; and
    wherein an average linear attenuation coefficient (LAC) value is determined from a distribution of a histogram of transmission data values for each MR coil in the plurality of coils and assigned to each respective MR coil.

20. A method of adjusting a patient attenuation correction (AC) map for correcting attenuation in nuclear scan data, including:
    receiving coil identification information that identifies a coil for which an AC map template is desired;
    retrieving the identified AC map template from a template library stored in a memory;
    adapting the AC map template to conform to a contour of a patient in a patient image, wherein the AC map template is assigned an average linear attenuation coefficient (LAC) value that is determined from a distribution of a histogram of transmission data values for the identified coil;
    inserting the adapted AC map template into a patient-specific attenuation correction (AC) map to generate a final AC map; and
    correcting attenuation when reconstructing nuclear scan data of a patient to generate an attenuation-corrected nuclear image of the patient.

21. The method according to claim 20, wherein adapting the AC map template to conform to a contour of a patient image is performed using a fiducial marker technique.

22. The method according to claim 20, wherein adapting the AC map template to conform to a contour of a patient image is performed using an edge-detection technique.

* * * * *